US00PP31689P3

(12) United States Plant Patent
de Jongh

(10) Patent No.: US PP31,689 P3
(45) Date of Patent: Apr. 21, 2020

(54) ***RUBUS* PLANT NAMED '16TP4'**

(50) Latin Name: ***Rubus* hybrid**
Varietal Denomination: 16TP4

(71) Applicant: Beekers Berries Breeding B.V., Breda (NL)

(72) Inventor: Johannes Adrianus Petrus de Jongh, Etten-Leur (NL)

(73) Assignee: BEEKERS BERRIES BREEDING BV, Breda (NL)

( * ) Notice: Subject to any disclaimer, the term of this patent is extended or adjusted under 35 U.S.C. 154(b) by 0 days.

(21) Appl. No.: 15/999,994

(22) Filed: Sep. 7, 2018

(65) Prior Publication Data

US 2019/0082571 P1 Mar. 14, 2019

(30) Foreign Application Priority Data

Sep. 8, 2017 (QZ) ..... PBR 2017/2179

(51) Int. Cl.
*A01H 5/08* (2018.01)
*A01H 6/74* (2018.01)

(52) U.S. Cl.
USPC ..... Plt./203
CPC ..... *A01H 6/7499* (2018.05)

(58) Field of Classification Search
USPC ..... Plt./203
CPC ..... A01H 5/0887
See application file for complete search history.

*Primary Examiner* — Kent L Bell
(74) *Attorney, Agent, or Firm* — Penny J. Aguirre

(57) ABSTRACT

A new cultivar of *Rubus* named '16TP4' that is characterized by its thornless canes, its semi-upright plant habit, its 3 or 5 leaflets per leaf, its late flowering season, its berries that are 10 to 20 grams in weight, and its fruiting on floricanes only.

2 Drawing Sheets

Botanical classification: *Rubus* hybrid.
Cultivar designation: '16TP4'.

BACKGROUND OF THE INVENTION

The present invention relates to a new and distinct cultivar of blackberry plant, botanically of hybrid origin with *Rubus* hybrid and other species in its ancestry. '16TP4' will be referred to hereinafter by its cultivar name, '16TP4'. '16TP4' is a new blackberry plant grown for fruit production.

'16TP4' was discovered by the Inventor as a chance seedling in spring of 2016 amongst seedlings that were grown from an unnamed blackberry plant in Etten-Leur, The Netherlands.

Asexual propagation of the new cultivar was first accomplished by the Inventor by stem cuttings in spring of 2016 in Etten-Leur, The Netherlands. Asexual propagation of the new cultivar by root cuttings, stem cuttings, and tissue culture using meristem tissue has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish '16TP4' as a new and unique cultivar of *Rubus*.

1. '16TP4' exhibits thornless canes.
2. '16TP4' exhibits a semi-upright plant habit.
3. '16TP4' exhibits 3 or 5 leaflets per leaf.
4. '16TP4' exhibits a late flowering season.

5. '16TP4' exhibits berries that are 10 to 20 grams in weight.
6. '16TP4' exhibits fruiting on floricanes only.

'16TP4' can be compared to the cultivars 'Loch Ness' (U.S. Plant Pat. No. 6,782) and 'Loch Tay' (not patented). 'Loch Ness' and 'Loch Tay' are similar to '16TP4' in fruiting on floricanes and in having thornless canes. 'Loch Ness' differs from '16TP4' in having fruit that are smaller, laterals that are shorter, leaves that are smaller, and less fruit per lateral. 'Loch Tay' differs from '16TP4' in flowering much earlier, in having much smaller fruit, in being less productive, and canes that are thinner.

BRIEF DESCRIPTION OF THE DRAWINGS

The accompanying colored photographs illustrate the overall appearance and distinct characteristics of the new *Rubus*. The photographs were taken of plants 21 months in age as grown in an unheated greenhouse in 19-cm containers in Made, the Netherlands.

The photograph in FIG. 1 provides a view of plants of '16TP4'.

Figure 1:
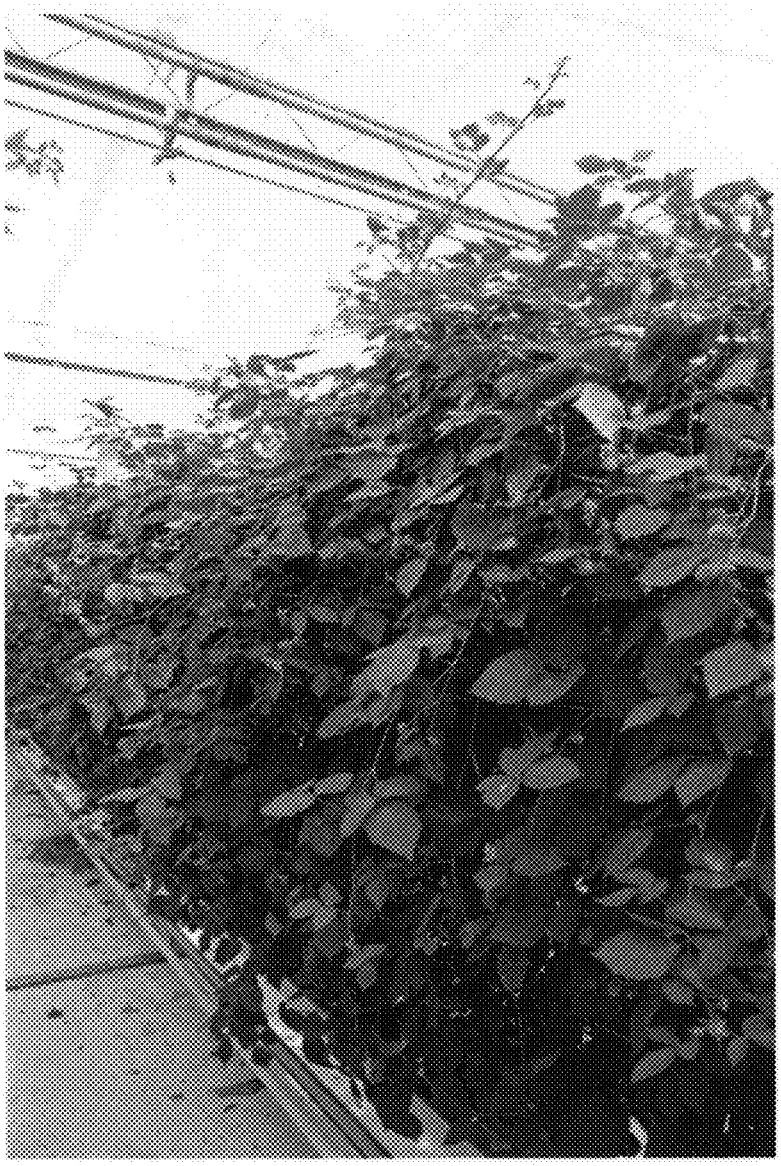
Figure 2:
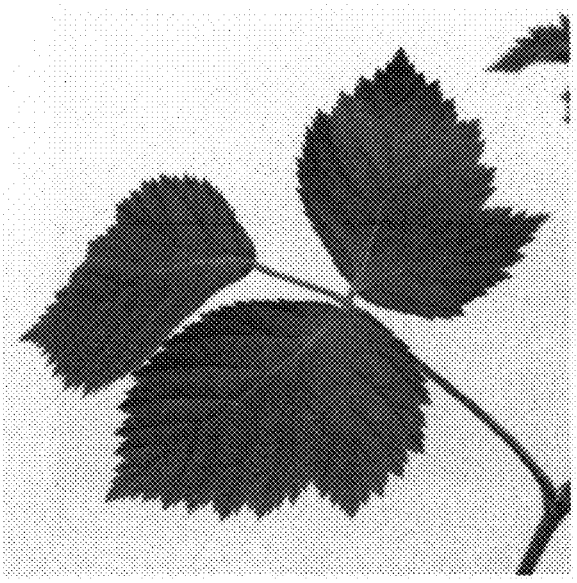

The photograph in FIG. 2 provides a close-up view of a leaf of '16TP4'.

Figure 3:
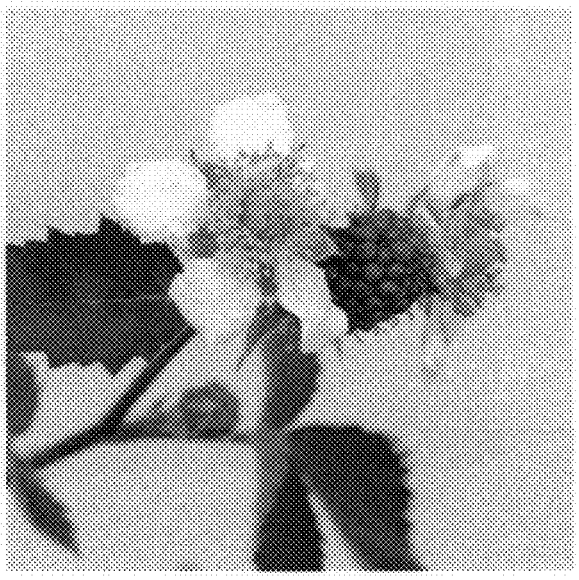

The photograph in FIG. 3 provides a close-up view of the flowers of '16TP4'.

Figure 4:
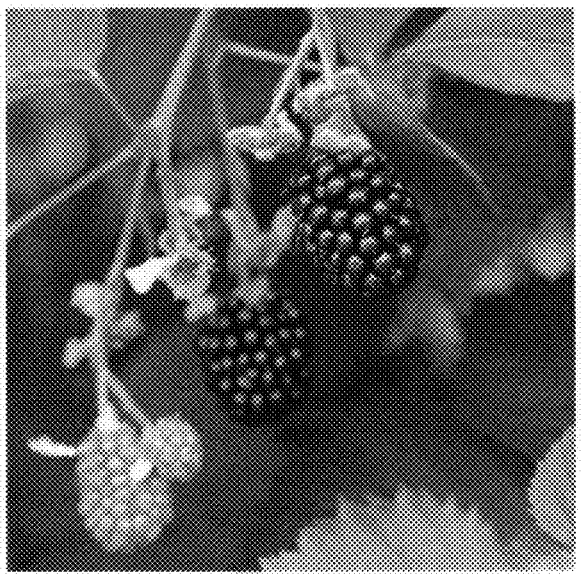

The photograph in FIG. 4 provides a close-up view of the fruit of '16TP4'.

The colors in the photographs are as close as possible with the photographic and printing technology utilized. The colors in the photograph may differ slightly from the color values cited in the detailed botanical description, which accurately describe the colors of the new *Rubus*.

DETAILED BOTANICAL DESCRIPTION OF THE PLANT

The following is a detailed description of plants 21 months in age as grown in an unheated greenhouse in 19-cm containers in Made, the Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type.*—Fruit producing perennial.

*Plant habit.*—Semi-upright.

*Height and spread.*—An average of 1.8 cm in height and 1.38 cm in spread as a 21-month old plant as grown in a 21-cm container.

*Hardiness.*—This trait has not been fully characterized in a range of cold weather climates but the plants can successfully grow in central Europe (U. K. Hardiness Zone 7).

*Diseases and pests.*—No resistance or susceptibility to pests or diseases has been observed.

*Root description.*—Fibrous and vigorous.

*Branching habit.*—Freely branching; an average of 5 main canes and 26 lateral stems per plant.

*Propagation.*—Root cuttings, stem cuttings or tissue culture.

*Root development.*—An average of 2 weeks to initiate roots, an average of 7 months to fully develop as a plant with 5 canes that are 2 m in height.

*Growth rate.*—Very vigorous.

Cane description (floricanes):

*Cane size.*—An average of 2.2 m in length and an average of 6 mm in width.

*Cane internode length.*—10 cm.

*Cane shape and aspect.*—Angled, lateral branches held at an average of 55° to 65° to vertical of main branch.

*Cane strength.*—Strong.

*Cane color.*—The new canes are N199B and heavily suffused with 146B, mature canes 144A with internodes 144A, older stems 146B.

*Stem surface.*—Glossy, thornless, moderately to densely covered with soft hairs; about 1 mm in length and too fine to measure color.

*Stipules.*—2 per petiole, leafy; narrow elliptic in shape, an average of 1.5 cm in length and 2.5 mm in width, apex narrow acute, cuneate base, upper surface a color between 141A and 147B, lower surface 147A, both surfaces covered with adpressed hairs; an average of 1 mm in length and transparent and NN155D in color.

Cane description (primocanes): Develops in spring and initiate flower buds in autumn and develops into the floricane the following season that flowers and produces fruit, the botanical description are similar in all aspects to the floricanes with the exception of producing flowers an fruit.

Foliage description:

*Time of vegetative bud burst.*—Early to mid season.

*Leaf shape.*—Broadly cordate in overall form.

*Leaf arrangement.*—Alternate.

*Leaf division.*—Compound; 3 to 5 leaflets.

*Leaf attachment.*—Petiolate.

*Leaf orientation.*—Flat to slightly concave.

*Leaf size.*—An average of 16.3 cm in length and 9.5 cm in width.

*Leaflet shape.*—Broad ovate to near rhomboidal.

*Leaflet base.*—Rounded.

*Leaflet apex.*—Broad apiculate.

*Leaflet venation.*—Pinnate, 144A on upper surface and 145B on lower surface.

*Leaflet margins.*—Bi-serrate, basal leaflets occasionally with one lobe; shallow with sinus divergent.

*Leaflet arrangement.*—One terminal and 1 to 2 lateral pairs.

*Leaflet attachment.*—Primarily sessile.

*Leaflet surface.*—Upper and lower surface rugose, moderately pubescent on upper surface and densely pubescent on lower surface, hairs 1 mm in length, transparent, and about NN155D in color.

*Leaflet color.*—Young leaf: upper surface a color between 143A and 146B, lower surface 143C, mature leaf: upper surface 144A, lower surface 145B, no change in fall.

*Leaflet size.*—An average of 9.5 cm in length and 7.9 cm in width.

*Petioles.*—Round in shape, an average of 10 cm in length and 2 mm in width, color; upper surface 143A, lower surface 144B, strong, both surfaces pubescent on both surfaces; hairs 1 mm in length, transparent, and NN155D in color.

*Rachis.*—Round in shape, an average of 3 cm in length and 1.7 mm in width, color; upper surface 143A, lower surface 144B, both surfaces pubescent on both surfaces; hairs 1 mm in length, transparent, and NN155D in color.

Inflorescence description:

*Blooming period.*—As a floricane; late season; flowering for 8 weeks in summer in The Netherlands.

*Inflorescence.*—Panicle, an average of 14.6 cm in length, an average of 11.4 cm in diameter.

*Peduncle.*—Flattened in shape, an average of 11 cm in length and 3 mm in width, held straight vertical stem, color upper surface 146A and lower surface 146C, moderate to strong in strength, surface moderately glossy with soft thin hairs 1 mm in length and NN155D in color.

*Pedicels.*—Round in shape, color 144A, an average of 1.9 cm in length and 1.5 mm in width, surface moderately glossy with soft thin hairs 1 mm in length and NN155D in color, moderate to strong in strength, held at a 40° angle to peduncle.

*Flower buds.*—Nearly orbicular in shape, average of 8 mm in length and 9 mm in diameter, color immature sepals 143A to 143B and petals NN155D, surface petal portion glabrous, sepal portion covered with soft hairs 0.5 mm in length and NN155D in color.

*Flower type.*—Rotate, single.

*Flower number.*—An average of 13 per inflorescence, 340 per plant.

*Flower fragrance.*—Faint, somewhat moldy.

*Flower size.*—Average of 3.6 cm in height and diameter.

*Sepals.*—Five, an average of 7 mm in length and 5 mm in width, broadly ovate to near deltoid in shape, base broad cuneate, apex aristate, entire margin, color when opening and mature 146D on upper surface and 143A to 143B on lower surface, both surfaces densely covered with hairs; 1 mm in length and NN155D in color, upper surface matte, lower surface moderately glossy.

*Petals.*—Five, an average of 1.7 cm in length and 1 cm in width, base cuneate, apex obtuse, entire margin with medium undulation, glabrous and matte on upper and lower surfaces, color; when opening upper and lower surface NN155D and slightly tinged with 157C at base, when fully open upper and lower surface NN155D and slightly tinged with 157D at base.

*Floral bracts.*—2 at base of pedicel, leafy; narrow elliptic in shape, an average of 1 cm in length and 2 mm in width, apex narrow acute, cuneate base, entire margin, color both surfaces 143A with centers 144B to 144C, lower surface 147A, both surfaces covered with adpressed hairs; an average of 1 mm in length and transparent and NN155D in color.

*Androecium.*—An average of 120 stamens, filaments 4 mm in length and 157D in color, anthers 1 mm in length, 0.8 mm in width, and a color between 145C and 150D, pollen low to moderate in quantity and 155B in color.

*Gynoecium.*—An average of 90 pistils, 1.8 mm in length, stigmas cup-shaped, 0.5 mm in length and diameter, 145C in color, styles 1.3 mm in length and 145C in color, ovary 144A in color.

Fruit description:

*Fruit number.*—An average of 340 per plant.

*Fruit size.*—An average of 4.1 cm in length and 2.8 mm in diameter.

*Fruit shape.*—Oblong.

*Fruit texture.*—Smooth, glossy, glabrous except for persistent styles 2 mm in length and 164A to 164B in color.

*Druplets.*—An average of 67 per berry, 5 to 7 mm in length and width.

*Fruit size.*—Up to 4 cm in length and an average of 3 cm in width.

*Fruit maturity date.*—Late summer on floricanes.

*Seed.*—Oblong in shape, average of 5 (ranges from seedless to 10 per fruit), 3.5 mm in length, 2 mm in width, 199C to 199D in color and spotted with 200B.

*Cropping frequency.*—Annually, on floricanes.

*Harvest dates.*—Typically a first harvest date of April 18th and a last harvest date of July 1st when planted in a heated greenhouse on January 2nd in The Netherlands.

*Flavor.*—Pleasant, moderately sweet with an acidic aftertaste.

*Fruit weight.*—10 to 20 g/fruit.

*Brix.*—9 to 10.5.

*pH.*—3.5.

*Shelf life.*—An average of 7 days after picking.

*Market use.*—Fresh fruit.

It is claimed:

1. A new and distinct cultivar of *Rubus* plant named '16TP4' as herein illustrated and described.

* * * * *